United States Patent [19]

Winn et al.

[11] 4,234,594
[45] Nov. 18, 1980

[54] PYRAZOLYL AMINO IMIDAZOLINES AS ANTIHYPERTENSIVE AGENTS

[75] Inventors: Martin Winn, Deerfield; Carl W. Nordeen, Waukegan; David L. Arendsen, Libertyville, all of Ill.

[73] Assignee: Abbott Laboratories, North Chicago, Ill.

[21] Appl. No.: 36,884

[22] Filed: May 7, 1979

[51] Int. Cl.³ .................... A61K 31/40; A61K 31/47; A61K 31/415; A61K 31/435
[52] U.S. Cl. ................. 424/273 P; 424/256; 424/258; 424/263; 424/274
[58] Field of Search ............ 424/273 P, 263, 258, 424/256, 274; 548/316

[56] References Cited
U.S. PATENT DOCUMENTS 4,171,367  10/1979  Winn et al. .............. 424/273 P Primary Examiner—Douglas W. Robinson
Attorney, Agent, or Firm—Gildo E. Fato; Robert L. Niblack

[57] ABSTRACT

Described is a method of treating hypertensive by administering to mammalian patients compounds of the formula

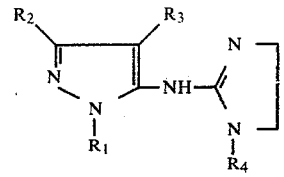

wherein $R_1$ and $R_2$ are hydrogen, loweralkyl, lowercycloalkyl, aralkyl, aryl, pyridyl, isoquinolyl, phthalazinyl, or aryl substituted by one or more hydrogen, halo, loweralkyl, lowercycloalkyl, haloloweralkyl, haloloweralkyl, aminosulfonyl, nitro, hydroxy, alkoxy, carboxy, alkoxycarbonyl, cycloalkoxy carbonyl, aminocarbonyl, diloweralkylaminocarbonyl or

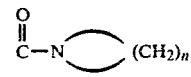

wherein
n is 4 or 5.
$R_3$ is hydrogen, halogen, loweralkyl or aryl, and
$R_4$ is hydrogen, acyl, amino or loweralkyl, and the pharmaceutically acceptable acid addition salts thereof.

9 Claims, No Drawings

PYRAZOLYL AMINO IMIDAZOLINES AS ANTIHYPERTENSIVE AGENTS

BACKGROUND OF THE INVENTION

Hypertension describes a symptom of several disease entities, both of known and unknown etiology, elevated blood pressure being the measurement indicating its presence. A persistently elevated blood pressure is considered a serious symptom. High blood pressure can be temporary or can result from known causes such as kidney or artery disease. While some types of hypertension respond only to surgery and in others sedatives may comprise the sole therapy, most forms of hypertension are treated by means of chemotherapy. Untreated hypertension produces risk of cardiovascular complications such as strokes, myocardial infraction and the like which lower the quality of life and life expectancy, whereas drug therapy can significantly improve the longevity of the hypertensive population. Chemical entities capable of lowering blood pressure in mammals such as the antihypertensive agents provided by the present invention, are consequently highly desirable.

DETAILED DESCRIPTION OF THE INVENTION

This invention relates to a method of treating hypertension in mammalian patients by administering compounds represented by the formula

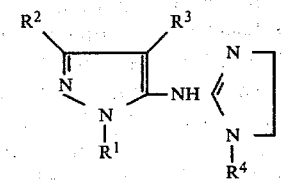

A wherein $R^1$ and $R^2$ are hydrogen, loweralkyl, lowercycloalkyl

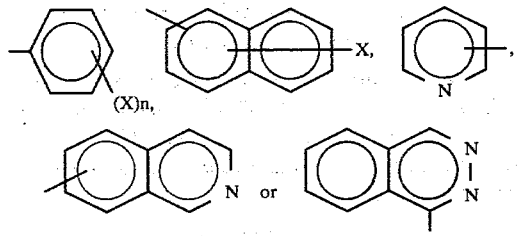

where X is H, halo, loweralkyl, lowercycloalkyl, haloalkyl, $SO_2NH_2$, $NO_2$, $NH_2$, OH, alkoxy, COOH, alkoxycarbonyl, cycloalkoxy carbonyl, aminocarbonyl, diloweralkylaminocarbonyl where n is 0, 1, 2 or 3

wherein m is 4 or 5, $R_3$ is H, halogen or aryl, and $R_4$ is H, acyl, amino or loweralkyl or the pharmaceutically acceptable acid addition salts thereof.

The term "loweralkyl" refers to straight or branched chain alkyl groups having from 1 to 6 carbon atoms, i.e., methyl, ethyl, n-propyl, iso-propyl, n-butyl, sec-butyl, tertbutyl, n-pentyl, n-hexyl, and the like.

The term "aryl" as used herein refers to phenyl and naphthyl.

The term "acyl", as used herein, refers to acyl groups represented by the formula

wherein R is loweralkyl, i.e., acetyl, propionyl, butyryl, and the like or phenyl.

The term "pharmaceutically acceptable salts" refers to non-toxic acid addition salts prepared by reacting the base with a suitable organic or inorganic acid. Representative salts include the hydrochloride, hydrobromide, sulfate, bisulfate, acetate, oxylate, valerate, oleate, palmitate, stearate, laurate, borate, benzoate, lactate, phosphate, tosylate, citrate, maleate, fumarate, succinate, tartate, and the like.

The compounds of this invention exhibit antihypertensive activity and are effective generally when administered to mammalian patients in dosages of from about 1 to 200 milligrams per kilogram (mg/kg) of body weight daily, either in single or divided doses over a 24 hour period.

The compounds of the present invention can be prepared by two methods, as illustrated below.

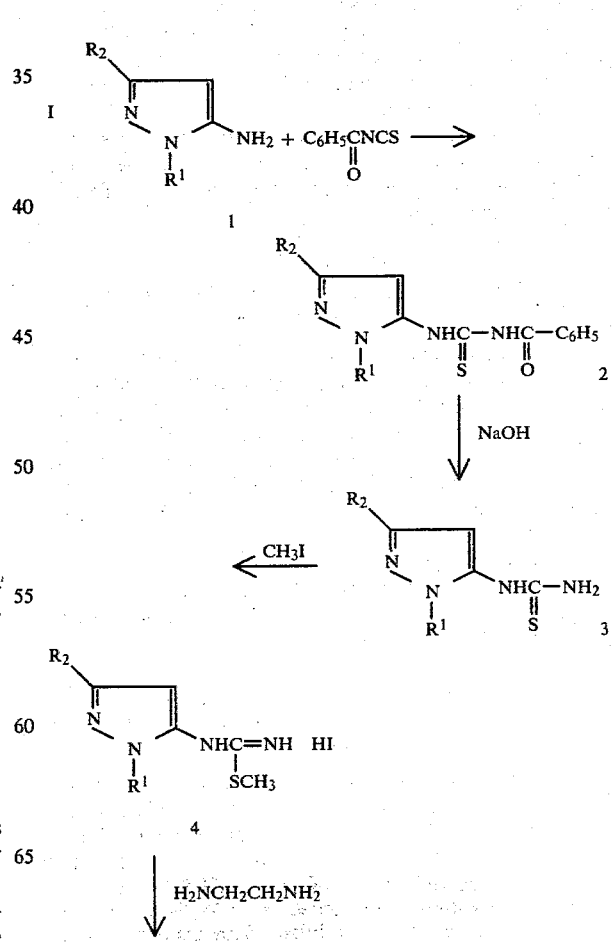

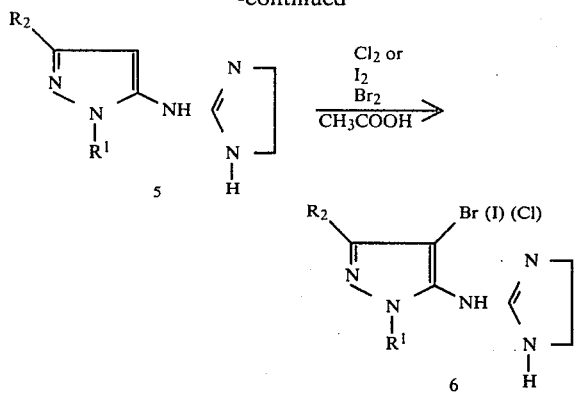

In the first method a 1,3-disubstituted-5-aminopyrazole (1) is reacted with benzoyl isothiocyanate to produce N(1,3-disubstituted-5-pyrazolyl)-$N^1$-benzoyl thiourea (2). This product reacts with sodium hydroxide to produce (1,3-disubstituted-5-pyrazolyl) thiourea (3) which in turn reacts with methyl iodide to produce N(1,3-disubstituted-5-pyrazolyl)-5-methyl isothiourea hydroiodide (4). This compound then reacts with ethylene diamine to produce 2-(1,3-disubstituted-5-pyrazolyl)amino-2-imidazoline (5), which is treated with a halogen ($Cl_2$, $Br_2$ or $I_2$) to produce 2(4-Halo-1,3-disubstituted-5-pyrazolyl)amino-2-imidazoline.

In the second method, compound (1) is reacted with 1-acetyl-2-imidazolidinone to produce 1-acetyl-2-(1,3-disubstituted 5-pyrazolyl)amino-2-imidazoline (7). The acetyl group is removed with HCl in methanol to produce the compound 5 which is halogenated as above to produce compound 6.

The preferred method of preparation is represented the second method, described above. Representative compounds which can be prepared are exemplified in the following examples.

EXAMPLE I

1-Acetyl-2(3-isopropyl-1-methyl-5-pyrazolyl) amino-2-imidazoline 5-amino-3-isopropyl-1-methyl pyrazole (described in British Pat. No. 1,057,740) (19.3 g) was dissolved in 180 ml. phosphorus oxychloride ($POCl_3$). 1-Acetyl-2-imidazolidinone (J. Chem Soc 1964, 178) (20.1 g) was added. This reaction mixture was stirred at 55° for 40 hr. The solvents were concentrated in vacuum, ice and methylene chloride were added and the mixture neutralized with 25% sodium hydroxide in water. The methylene chloride layer was dried over $MgSO_4$ and then concentrated and the residue crystallized from isopropyl alcohol and ether to give 12.73 g. of product, mp 145°–147° C.

EXAMPLE II

2(3-Isopropyl-1-methyl-5-pyrazolyl)-amino-2-imidazoline

1-Acetyl-2(3-isopropyl-1-methyl-5-pyrazolyl)-amino-2-imidazoline (6.21 g.), 120 ml. methanol and 2 drops concentrated hydrochloric acid were mixed and refluxed 16 hr. The solution was then concentrated and the residue treated with $CHCl_3$ and $KHCO_3$ solution. The $CHCl_3$ solution was dried over $MgSO_4$, concentrated and the residue crystallized from isopropyl alcohol and ether to give 4.50 g. of product, mp 163°–165° C.

Analyzed for $C_{10}H_{17}N_5$: theoretical; C=57.94, H=8.28, N=33.79. Found; C=57.83, H=8.45, N=33.58.

EXAMPLE III 2-(4-Bromo-3-isopropyl-1-methyl-5-pyrazolyl)amino-2-imidazoline hydrobromide 2(3-isopropyl-1-methyl-5-pyrazolyl)-amino-2-imidazoline (6.00 g.) was dissolved in 30 ml. acetic acid. A solution of 4.55 g. bromine in 10 ml. acetic acid was added dropwise, while cooling, until the color of $Br_2$ persisted. The solution was concentrated in vacuum and the residue crystallized from isopropyl alcohol to give 7.85 g. product, mp 225°–226° C., decomposed.

Analyzed for $C_{10}H_{17}Br_2N_5$: Theoretical; C=32.72, H=4.66, N=19.07. Found; C=32.78, H=4.72, N=19.24.

EXAMPLE IV

[1-(3-Methylbutyl)-3-methyl-5-pyrazolyl] thiourea 1-(3-methylbutyl)-3-methyl-5-aminopyrazole (British Pat. No. 1,057,740) (21.2 g.) was dissolved in 560 ml. benzene. Benzoyl isothiocyanate (21.19 g.) was added dropwise and then the solution was refluxed for 1 hr. The solvent was evaporated in vacuum to yield the intermediate benzoyl pyrazolyl thiourea. This compound was hydrolyzed by refluxing in 100 ml. 10% sodium hydroxide for 20 minutes. Then the mixture was cooled and acidified to a pH of 4 with hydrochloric acid. The resulting solid was filtered, washed with water, and then treated with concentrated ammonia. After stirring 5 minutes the solid was filtered, washed with water, and crystallized from an ethanol-hexane mixture to give 23.0 g. product, mp 173°–176° C.

EXAMPLE V

N[1-(3-Methylbutyl)-3-methyl-5-pyrazolyl]-S-methyl isothiourea hydroiodide

[1-(3-methylbutyl)-3-methyl-5-pyrazolyl] thiourea (23.0 g) was dissolved in 250 ml. ethanol and 15.62 g. methyl iodide and refluxed for 4 hours. The ethanol was concentrated in vacuum and ether added to get 29.3 g. product, mp 128°–131° C.

EXAMPLE VI

2[1-(3-Methylbutyl)-3-methyl-5-pyrazolyl] amino-2-imidazoline

N[1-(3-methylbutyl)-3-methyl-5-pyrazolyl]-S-methyl isothiourea hydroiodide (29.0 g.) was suspended in 160 ml. n-propyl alcohol. Ethylene diamine (10.2 g.) was added and the solution was refluxed 18 hrs. The solvent was concentrated in vacuum and the residue was treated with $KHCO_3$ in water. The resulting solid was recrystallized from $CHCl_3$-ether mixtures to obtain 14.3 g. product, mp 104°–106° C.

Analyzed for $C_{12}H_{21}N_5$: Theoretical; C=61.24, H=9.03, N=29.76. Found; C=61.40, H=9.33, N=29.69.

EXAMPLE VII

2[4-Bromo-1-(3-methylbutyl)-3-methyl-5-pyrazolyl]amino-2-imidazoline hydrochloride 2[1-(3-methylbutyl)-3-methyl-5-pyrazolyl] amino-2-imidazoline (6.00 g.) in 35 ml. acetic acid was treated with a solution of 4.10 g. bromine in 10 ml. acetic acid, added dropwise, the solution was then concentrated and the residue treated with chloroform, water, and potassium bicarbonate. The CHCl$_3$ phase was dried over MgSO$_4$ and concentrated. The residue was dissolved in isopropyl alcohol and acidified with HCl. On adding ether, 7.06 g. product, mp 180°–182° C. crystallized out.

Analyzed for $C_{12}H_{21}BrClN_5$: Theoretical; C=41.15, H=6.03, N=19.98. Found; C=41.19, H=6.21, N=20.33.

EXAMPLE VIII

1-Acetyl-2-(1-phenyl-5-pyrazolyl)-amino-2-imidazoline

5-Amino-1-phenylpyrazole (6.00 g.), and 1-acetyl-2-imidazolidinone (5.50 g.) were reacted as described in Example I to give 4.95 g. of product, mp 157°–159° C.

Analyzed for $C_{14}H_{15}N_5O$: Theoretical; C=60.40, H=5.85, N=25.11. Found; C=60.65, H=5.74, N=24.75.

EXAMPLE IX 2-(1-Phenyl-5-pyrazolyl)-amino-2-imidazoline

Acetyl-2(1-phenyl-5-pyrazolyl)-amino-2-imidazoline (15.1 g.) was treated with HCl in methanol as described in Example II to give 12.5 g. product mp 206°–208° C. The hydrochloride, made with HCl in isopropyl alcohol had a mp of 232°–234° C.

Analyzed for $C_{12}H_{14}ClN_5$: Theoretical; C=54.70, H=5.36, N=26.55. Found; C=54.91, H=5.41, N=26.69.

EXAMPLE X 2-(4-Bromo-1-phenyl-5-pyrazolyl)-amino-2-imidazoline hydrochloride 2-(1-phenyl-5-pyrazolyl)-amino-2-imidazoline (5.00 g.) and 3.85 g. bromine were reacted as described in Example VII to give 6.02 g. of product, mp 251°–253° C.

Analyzed for $C_{12}H_{13}BrClN_5$: Theoretical; C=42.02, H=3.83, N=20.50. Found; C=42.21, H=3.85, N=19.81.

EXAMPLE XI

1-Acetyl-2(1-isopropyl-3-methyl-5-pyrazolyl)amino-2-imidazoline 5-amino-1-isopropyl-3-methylpyrazole (J. Gen. Chem. USSR 31 234, 1961) (19.3 g.) and 1-acetyl-2-imidazolidinone (20.1 g.) were reacted as described in Example I to give 12.73 g. of product, mp 145°–147° C.

EXAMPLE XII 2-(1-Isopropyl-3-methyl-5-pyrazolyl) amino-2-imidazoline 1-acetyl-2-(1-isopropyl-3-methyl-5-pyrazolyl) amino-2-imidazoline (14.0 g.) was treated with HCl in methanol as described in Example II to give 9.05 g of product, mp 173°–175° C.

Analyzed for $C_{10}H_{17}N_5$: Theoretical; C=57.94, H=8.28, N=33.79. Found; C=57.76, H=8.44, N=33.93.

EXAMPLE XIII 2-(4-Bromo-1-isopropyl-3-methyl-5-pyrazolyl)amino-2-imidazoline hydrochloride 2-(1-isopropyl-3-methyl-5-pyrazolyl)amino-2-imidazoline (6.00 g.) was treated with 4.60 g. of bromine as described in Example VII to give 8.26 g. product, mp 235°–256° C.; decomposed.

Analyzed for $C_{10}H_{17}ClBrN_5$: Theoretical; C=37.21, H=5.32, N=21.70. Found; C=37.17, H=5.26, N=21.62.

EXAMPLE XIV 2-(1-Cyclohexyl-5-pyrazolyl)-amino-2-imidazoline 2-(1-phenyl-5-pyrazolyl)-amino-2-imidazoline (9.00 g.) in 250 ml. methanol was hydrogenated at 3 atmospheres and 60° C. over 5% Rh/Al$_2$O$_3$ catalyst. The catalyst was filtered, the solvent removed in vacuum and the residue crystallized from benzene to give 4.0 g. of product, mp 183°–185° C.

Analyzed for $C_{12}H_{19}N_5$: Theoretical; C=61.78, H=8.21, N=30.02. Found; C=61.63, H=8.33, N=29.63.

EXAMPLE XV 2-(4-Bromo-1-cyclohexyl-5-pyrazolyl)-amino-2-imidazoline hydrochloride 2-(1-cyclohexyl-5-pyrazolyl)-amino-2-imidazoline (6.40 g.) was treated with 14.30 g bromine as described in Example VII to give 8.10 g. product, mp 242°–244° C. decomposed.

Analyzed for $C_{12}H_{19}BrClN_5$: Theoretical; C=41.30, H=5.49, N=20.08. Found, C=41.18, H=5.09, N=19.65.

EXAMPLE XVI

5-Amino-1,3-di-isopropyl pyrazole 4-methyl-3-keto pentanitrile (13.0 g) (Can. J. Chem. 48, 2110, 1970) (13.0 g.), ispropyl hydrazine (10.0 g.) and 50 ml. ethanol were refluxed for 4 hrs. The solvent was removed in vacuum and the residue crystallized from cyclohexane and ether to produce 13.88 g. of product, mp 62°–65° C.

Analyzed for $C_9H_{17}N_3$: Theoretical; C=64.63, H=10.25, N=25.13. Found; C=64.67, H=10.51, N=25.40.

EXAMPLE XVII

1-Acetyl-2-(1,3-di-isopropyl-5-pyrazolyl) amino-2-imidazoline

5-Amino-1,3-di-isopropyl pyrazole (13.5 g.) and 1-acetyl-2-imidazolidinone (12.2 g.) were reacted as described in Example I to give 13.01 g. of product, mp 139°–140° C.

EXAMPLE XVIII 2-(1,3-Di-isopropyl-5-pyrazolyl)-amino-2-imidazoline

1-Acetyl-3-(1,3-di-isopropyl-5-pyrazolyl)amino-2-imidazoline (13.0 g.) was treated with HCl in methanol as described in Example II to give 6.60 g. of product, mp 159°–161° C.

Analyzed for $C_{12}H_{21}N_5$: Theoretical; C=61.24, H=9.00, N=29.76. Found; C=61.04, H=9.21, N=29.93.

EXAMPLE XIX 2-(4-Bromo-1,3-di-isopropyl-5-pyrazolyl)amino-2-imidazoline hydrobromide 2-(1,3-Di-isopropyl-5-pyrazolyl)-amino-2-imidazoline (2.00 g.) was treated with 1.5 g. bromine as described in Example III to give 2.61 g. of product, mp 220°–221° C., decomposed.

Analyzed for $C_{12}H_{21}Br_2N_5$: Theoretical; C=36.47, H=5.35, N=17.73, Br=40.45. Found; C=36.71, H=5.56, N=17.60, Br=40.36.

EXAMPLE XX (1,3-Diphenyl-5-pyrazolyl) thiourea 1,3-Diphenyl-5-amino pyrazole (117.5 g.) and benzoyl isothiocyanate (89.65 g.) were reacted as described in Example IV to give 119.8 g. of product, mp 198°–201° C.

EXAMPLE XXI

N-(1,3-Diphenyl-5-pyrazolyl)-S-methyl isothiourea hydroiodide (1,3-Diphenyl-5-pyrazolyl) thiourea (119.7 g.) and 63.9 g. methyl iodide were reacted as described in Example V to give 156.1 g. of product, mp 178°–182° C.

EXAMPLE XXII

2(1,3-Diphenyl-5-pyrazolyl) amino-2-imidazoline

N(1,3-Diphenyl-5-pyrazolyl)-S-methyl isothiourea hydroiodide (43.6 g.) and ethylene diamine (12.0 g.) were reacted as described in Example VI to give 26.0 g. of the product, mp 228°–230° C.

Analyzed for $C_{18}H_{17}N_5$: Theoretical; C=71.29, H=5.61, N=23.10. Found; C=71.20, H=5.64, N=23.16.

EXAMPLE XXIII

2(4-Bromo-1,3-diphenyl-5-pyrazolyl) amino-2-imidazoline hydrobromide

2(1,3-diphenyl-5-pyrazolyl) amino-2-imidazoline (6.0 g.) was treated with 3.2 g. bromine as described in Example III to give 8.85 g. of the product, mp 273° C., decomposed.

Analyzed for $C_{18}H_{17}Br_2N_5$: Theoretical; C=46.80, H=3.71, N=15.12. Found; C=47.19, H=3.83, N=14.98.

EXAMPLE XXIV (1,3-Dimethyl-5-pyrazolyl) thiourea 1,3-Dimethyl-5-amino pyrazole (111.0 g.) and benzoyl iso thiocyanate (180.0 g.) were reacted as described in Example IV to give 110.3 g. of the product, mp 221°–224° C.

EXAMPLE XXV

N(1,3-Dimethyl-5-pyrazolyl)-S-methyl isothiourea hydroiodide (1,3-Dimethyl-5-pyrazolyl) thiourea (17.0 g) and 14.2 g methyl iodide were reacted as described in Example V to give 18.0 g. of the product, mp 158°–161° C.

Analyzed for $C_7H_{13}IN_4S$: Theoretical; C=26.92, H=4.16, N=17.94. Found; C=27.20, H=4.31, N=18.07.

EXAMPLE XXVI

2(1,3-Dimethyl-5-pyrazolyl) amino-2-imidazoline

N-(1,3-Dimethyl-5-pyrazolo)-S-methyl isothiourea hydroiodide (18.0 g.) and ethylene diamine (7.0 g.) were reacted as described in Example VI to give 7.60 g. of the product, mp 167°–169° C.

Analyzed for $C_8H_{13}N_5$: Theoretical; C=53.63, H=7.26, N=39.10. Found; C=53.58, H=7.36, N=39.11.

EXAMPLE XXVII

2(4-Bromo-1,3-dimethyl-5-pyrazolyl)-amino-2-imidazoline

2(1,3-Dimethyl-5-pyrazolyl)amino-2-imidazoline (13.25 g.) was treated with 12.8 g. bromine as described in Example III. The product was isolated as the base, 16.15 g. mp 230°–232° C.

Analyzed for $C_8H_{12}BrN_5$: Theoretical; C=37.21, H=4.65, N=27.13. Found; C=37.35, H=4.69, N=26.92.

EXAMPLE XXVIII

2(1,3-Dimethyl-4-iodo-5-pyrazolyl)-amino-2-imidazoline

2(1,3-Dimethyl-5-pyrazolyl) amino-2-imidazoline (8.95 g.) and 13.86 g. iodine was dissolved in 100 ml. acetic acid and stirred 16 hrs. at room temperature. The acetic acid was evaporated and sodium carbonate in water was added. The resulting solid was washed with water, and sodium sulfite solution and then crystallized from methanol to yield 6.85 g. of product, mp 226°–227° C.

Analyzed for $C_8H_{12}IN_5$: Theoretical; C=31.48, H=3.93, N=22.95. Found; C=31.37, H=3.98, N=23.10.

EXAMPLE XXIX

1-Acetyl-2(1-methyl-5-pyrazolyl) amino-2-imidazoline

5-Amino-1-methyl pyrazole hydrochloride (mp 143-145, from base described in Ber. 98, 3374, 1965) (40.0 g.) and 1-acetyl-2-imidazolinone (43.0 g.) were reacted as described in Example I to give 42.4 g. product mp 158°–166° (crystallized from CH₃CN)

Analyzed for $C_9H_{13}N_5O$: Theoretical; C=52.16, H=6.32, N=33.80. Found; C=52.35, H=6.46, N=33.61.

EXAMPLE XXX

2(1-methyl-5-pyrazolyl) amino-2-imidazoline hydrochloride

1-Acetyl-2(1-methyl-5-pyrazolyl)amino-2-imidazoline (37.4 g.) was treated with HCl in methanol as described in Example II to give 25.9 g. product mp 204–208 which was converted to the hydrochloride salt mp 187°–189°.

Analyzed for $C_9H_{11}N_5 \cdot HCl$: Theoretical; C=41.69, H=6.00, N=34.83. Found; C=41.79, H=6.18, N=34.76.

EXAMPLE XXXI

2(4-Bromo-1-methyl-5-pyrazolyl) amino-2-imidazoline hydrochloride

2(1-Methyl-5-pyrazolyl)amino-2-imidazoline (4.00 g.) was treated with 4.25 g. bromine as described in example VII to give 5.73 g. of product mp 225°–228°.

Analyzed for $C_7H_{10}BrN_5 \cdot HCl$: Theoretical; C=29.97, H=3.95, N=24.96. Found; C=30.13, H=3.99, N=24.62.

EXAMPLE XXXII

2(4-Chloro-1-methyl-5-pyrazolyl) amino-2-imidazoline hydrochloride

2(1-Methyl-5-pyrazolyl) amino-2-imidazoline (15.74 g.) was treated with 2.60 g. chlorine gas in 30 ml. acetic acid, while cooling in ice, by the method of Example VII to give 6.34 g. mp 254°–257°.

Analyzed for $C_7H_{10}ClN_5 \cdot HCl$: Theoretical; C=35.61, H=4.69, N=29.66. Found; C=35.79, H=4.83, N=29.43.

EXAMPLE XXXIII

5-Amino-1,3,4-trimethyl pyrazole hydrochloride

2-Methyl-3-keto-butyronitrile (J. Am. Chem. Soc. 79, 723, 1957) (25.25 g.) in 120 ml. ethanol was treated with 15 g. methylhydrazine while cooling. The solution was refluxed 3 hours then concentrated in vacuum, benzene added and the solution concentrated again. Ether was added to give 29.12 g. mp 70-106 of base (contained $H_2O$). This was converted to the hydrochloride with HCl in isopropyl alcohol. HCl had mp 286°–288°.

Analyzed for $C_6H_{11}N_3 \cdot HCl$: Theoretical; C=44.59, H=7.48, N=26.00. Found; C=44.40, H=7.63, N=25.73.

EXAMPLE XXXIV

1-Acetyl-2(1,3,4-trimethyl-5-pyrazolyl) amino-2-imidazoline

5-Amino-1,3,4-trimethyl pyrazole hydrochloride (8.00 g.) and 1-acetyl-2-imidazolinone (7.05 g.) were reacted as described in Example I to give 7.90 g. mp 212°–215° (crystallized from $CH_3CN$)

Analyzed for $C_{11}H_{17}N_5O$: Theoretical; C=56.15, H=7.28, N=29.77. Found; C=55.91, H=7.19, N=29.57.

EXAMPLE XXXV

2(1,3,4-Trimethyl-5-pyrazolyl) amino-2-imidazoline

1-Acetyl-2(1,3,4-trimethyl-5-pyrazolyl) amino-2-imidazoline (29.6 g.) was treated with HCl in methanol as described in Example II to give 21.70 g. product (crystallized from $CH_3CN$)

Analyzed for $C_9H_{15}N_5$: Theoretical; C=55.93, H=7.82, N=36.24. Found; C=56.24, H=7.95, N=36.16.

EXAMPLE XXXVI

1-Acetyl-2[1-(2-chlorophenyl)-5-pyrazolyl] amino-2-imidazoline

5-Amino-1(2-chlorophenyl) pyrazole hydrochloride (Farmaco, 22, 68, 1967) (20.5 g.) and 1-acetyl-2-imidazolinone (12.6 g.) were reacted as described in Example I to give 17.11 g. product mp 179°–181° (crystallized from $CH_3CN$)

Analyzed for $C_{14}H_{14}ClN_5O$: Theoretical; C=55.36, H=4.65, N=23.06. Found; C=55.96, H=4.64, N=23.42.

EXAMPLE XXXVII

2[1-(2-chlorophenyl)-5-pyrazolyl] amino-2-imidazoline

1-Acetyl-2[1-(2-chlorophenyl)-5-pyrazolyl] amino-2-imidazoline (14.0 g.) was treated with HCl in methanol as described in Example II to give 11.10 g. product mp 185°–188° (crystallized from $CH_3CN$)

Analyzed for $C_{12}H_{12}ClN_5$: Theoretical; C=55.07, N=4.62, N=26.76. Found; C=55.36, H=4.56, N=26.92.

EXAMPLE XXXVIII

1-Acetyl-2(1,4-dimethyl-5-pyrazolyl)amino-2-imidazoline 5-amino-1,4-dimethyl pyrazole hydrochloride (Z. Chem. 388, 1970) (5.72 g.) and 1-acetyl-2-imidazolinone (5.54 g.) were reacted as described in Example I to give 4.723 g. product mp 199°–202° (crystallized from $CH_3CN$)

Analyzed for $C_{10}H_{15}N_5O$: Theoretical; C=54.28, H=6.83, N=31.66. Found; C=54.75, H=6.93; N=31.24.

EXAMPLE XXXIX

2(1,4-Dimethyl)-5-pyrazolyl) amino-2-imidazoline

1-Acetyl-2(1,4-dimethyl-5-pyrazolyl) amino-2-imidazoline (4.72 g.) was treated with HCl in methanol as described in Example II to give 3.348 g. product mp 200°–202° (crystallized from $CH_3CN$)

Analyzed for $C_8H_{13}N_5$: Theoretical; C=53.63, H=7.26, N=39.10. Found; C=54.00, H=7.62, N=39.20.

EXAMPLE XL

1-Acetyl-2(3-methyl-1-phenyl-5-pyrazolyl) amino-2-imidazoline

5-Amino-3-methyl-1-phenyl pyrazole hydrochloride (37.8 g.) and -1-acetyl-2-imidazoline (27.4 g.) were reacted as described in Example I to give 35.4 g. product. mp 153°–162° (crystallized from $CH_3CN$)

EXAMPLE XLI

2(3-Methyl-1-phenyl-5-pyrazolyl)amino-2-imidazoline hydrochloride

1-Acetyl-2-(3-methyl-1-phenyl-5-pyrazolyl) amino-2-imidazoline (35.0 g.) was treated with HCl in methanol as described in Example II to give 28.7 g. product as the hydrochloride. mp 182°–184°

Analyzed for $C_{13}H_{15}N_5 \cdot HCl$: Theoretical; C=56.22, H=5.81; N=25.21. Found; C=56.24, H=5.83, N=25.08.

EXAMPLE XLII

2(3-Ethyl-1-methyl-5-pyrazolyl) amino-2-imidazoline hydrochloride

5-Amino-3-ethyl-1-methyl pyrazole (British Pat. No. 863,060) (35.2 g.) and 1-acetyl-2-imidazolinone (43.2 g.) were reacted as described in Example I to give 1-acetyl-2-(3-ethyl-1-methyl-5-pyrazolyl) amino-2-imidazoline which was de-acetylated without purification by the method of Example II giving 39.3 g. product. mp 160°–162°

Analyzed for $C_9H_{15}N_5\cdot HCl$: Theoretical; C=47.06, H=7.02, N=30.49. Found; C=46.89, H=7.01, N=30.29.

EXAMPLE XLIII

5-Amino-1-(4-fluorophenyl)-3-methyl-pyrazole

4-Fluorophenylhydrazine HCl (60.0 g.) 175 ml. water, 70 ml. concentrated hydrochloric acid and 28.8 g. 3-amino-2-butene nitrile were refluxed one hour. The solution was cooled and made basic with concentrated ammonia. The solid was filtered and crystallized from ether to get 51.05 g. product, mp 108°–110°, which was converted to the HCl salt mp 227°–229°

Analyzed for $C_{10}H_{10}FN_3\cdot HCl$: Theoretical; C=52.76, H=4.87, N=18.47. Found; C=52.96, H=4.87, N=18.36.

EXAMPLE XLIV

1-Acetyl-2[1-(4-fluorophenyl)-3-methyl-5-pyrazolyl] amino-2-imidazoline

5-Amino-1-(4-fluorophenyl)-3-methylpyrazole (25 g.) and 1-acetyl-2-imidazolinone (20.2 g.) were reacted as described in Example I to give 21.97 g. product, mp 189°–191°

Analyzed for $C_{15}H_{16}FN_5O$: Theoretical; C=59.79, H=5.31, N=23.24. Found; C=59.96, H=5.42, N=23.66.

EXAMPLE XLV

2[1-(4-Fluorophenyl)-3-methyl-5-pyrazolyl] amino-2-imidazoline

1-Acetyl-2[1-(4-fluorophenyl)-3-methyl-5-pyrazolyl] amino-2-imidazoline (21.0 g.) was treated with HCl in methanol as described in Example II to give 7.503 g. mp 213°–215°

Analyzed for $C_{13}H_{14}FN_5$: Theoretical; C=60.22, H=5.44, N=27.01. Found; C=59.94, H=5.54, N=26.98.

EXAMPLE XLVI

5-Amino-1-(4-fluorophenyl)-pyrazole hydrochloride

4-Fluorophenylhydrazine was converted to this product by the method described in Farmaco 22, 68, 1967. mp of HCl salt, 201°–210°

Analyzed for $C_9H_8FN_3\cdot HCl$: Theoretical; C=50.60, H=4.24, N=19.67. Found; C=50.56, H=4.25, N=19.75.

EXAMPLE XLVII

1-Acetyl-2[1-(4-fluorophenyl)-5-pyrazolyl]amino-2-imidazoline

5-Amino-1-(4-fluorophenyl)pyrazole HCl (21 g.) and 1-acetyl-2-imidazolinone (15.4 g.) were reacted as described in Example I to give 20.76 g. product. mp 162°–164°

Analyzed for $C_{14}H_{14}FN_5O$: Theoretical; C=58.53, H=4.91, N=24.37. Found; C=58.61, H=4.98, N=24.75.

EXAMPLE XLVIII

2[1-(4-fluorophenyl)-5-pyrazolyl] amino-2-imidazoline

1-Acetyl-2[1-(4-fluorophenyl)-5-pyrazolyl] amino-2-imidazoline (17.13 g.) was treated with HCl in methanol as described in Example II to give 12.06 g. product, mp 195°–197°

Analyzed for $C_{12}H_{12}FN_5$: Theoretical; C=58.77, H=4.93, N=28.55. Found; C=58.74, H=4.98, N=28.60.

EXAMPLE XLIX

1-Benzoyl-2(1,3-dimethyl-5-pyrazolyl) amino-2-imidazoline 5-amino-1,3-dimethylpyrazole (20.0 g.) and 1-benzoyl-2-imidazolinone (British Pat. No. 1,392,849) (28.4 g.) were reacted as described in Example I to give 22.02 g. product. mp 147°–149°

Analyzed for $C_{15}H_{17}N_5O$: Theoretical; C=63.58, H=6.05, N=24.72. Found; C=63.51, H=6.06, N=24.65.

EXAMPLE L

5-Amino-1(3-trifluoromethylphenyl)-3-methylpyrazole hydrochloride

3-Trifluoromethylphenyl hydrazine (Tetrahedron, 1960, 69) (25.0 g.) was reacted with 3-amino-2-butene nitrile (12.7 g.) as described in Example XLIII to give 36.1 g. product as HCl salt, mp 222°–226°.

Analyzed for $C_{11}H_{10}F_3N_3\cdot HCl$: Theoretical; C=47.58, H=3.99, N=15.13. Found; C=47.88, H=4.13, N=14.78.

EXAMPLE LI

1-Acetyl-2[1-(3-trifluoromethylphenyl)-3-methyl-5-pyrazolyl] amino-2-imidazoline 5-Amino-1-(3-trifluoromethylphenyl)-3-methyl pyrazole HCl (20.0 g.) and 1-acetyl-3-imidazolinone (11.1 g.) were reacted as described in Example I to give 15.0 g. product. mp 173°–175°

Analyzed for $C_{16}H_{16}F_3N_5O$: Theoretical; C=54.70, H=4.59, N=19.93. Found; C=54.77, H=4.66, N=19.93.

EXAMPLE LII

2[1-(3-Trifluoromethylphenyl)-3-methyl-5-pyrazolyl] amino-2-imidazoline hydrochloride 1-Acetyl-2[1-(3-Trifluoromethylphenyl)-3-methyl-5-pyrazolyl] amino-2-imidazoline (13.0 g.) was treated with HCl in methanol as described in Example II to give 10.12 g. of product as the HCl salt, mp 205°–206°.

Analyzed for $C_{14}H_{14}F_3N_5\cdot HCl$: Theoretical; C=48.63, H=4.37, N=20.25. Found; C=48.45, H=4.48, N=20.08.

EXAMPLE LIII

5-Amino-1-(3-Trifluoromethylphenyl) pyrazole

3-Trifluoromethylphenyl hydrazine was converted to this product by the method described in Farmaco 22 68, 1967, mp 77°–79°.

Analyzed for $C_{10}H_8F_3N_3$: Theoretical; C=52.87, H=3.55, N=18.49. Found; C=53.13, H=3.54, N=18.67.

EXAMPLE LIV

1-Acetyl-2[1-(3-Trifluoromethylphenyl)-5-pyrazolyl] amino-2-imidazoline

5-Amino-1-(3-trifluoromethylphenyl) pyrazole (19.0 g.) and 1-acetyl-2-imidazolinone (12.9 g.) were reacted as described in Example I to give 16.85 g. product, mp 194°–197°.

EXAMPLE LV

2-[1-(3-Trifluoromethylphenyl)-5-pyrazolyl] amino-2-imidazoline hydrochloride

1-Acetyl-2-[1-(3-Trifluoromethylphenyl)-5-pyrazolyl] amino-2-imidazoline (14.5 g.) was treated with HCl in methanol as described in Example II to give 10.69 g. product as the HCl salt, mp 151°-153°.

Analyzed for $C_{13}H_{12}F_3N_3HCl$: Theoretical; C=47.07, H=3.95, N=21.11. Found; C=47.39, H=4.04, N=20.93.

LVI

5-Amino-3-methyl-1-(1-naphthyl) pyrazole hydrochloride

1-Naphthyl hydrazine HCl (25.0 g.) was reacted with 3-amino-2-butene nitrile (10.6 g.) as described in Example XLIII to give 26.55 g. product as the HCl salt (crystallized from CH₃CN and other) mp 210°-213°.

Analyzed for $C_{14}H_{13}N_3HCl$: Theoretical; C=64.74, H=5.43, N=16.18. Found; C=64.45, H=5.31, N=16.10.

EXAMPLE LVII

1-Acetyl-2[1-(1-naphthyl)-3-methyl-5-pyrazolyl] amino-2-imidazoline

5-Amino-3-methyl-1-(1-naphthyl) pyrazole HCl (20.0 g.) and 1-acetyl-2-imidazolinine (12.0 g.) were reacted as described in Example I to give 19.80 g. product, mp 194°-195°

Analyzed for $C_{19}H_{19}N_5O$: Theoretical;

EXAMPLE LVIII

2[1-(1-Naphthyl)-3-methyl-5-pyrazolyl] amino-2-imidazoline

1-Acetyl-2[1-(1-naphthyl)-3-methyl-5-pyrazolyl] amino-2-imidazoline (15.27 g.) was treated with HCl in methanol as described in Example II to give 11.82 g. product, mp 221°-224°.

Analyzed for $C_{17}H_{17}N_5$: Theoretical,

EXAMPLE LVIX

5-Amino-3-methyl-1-(4-chloro-2-methylphenyl) pyrazole 5-chloro-2-methylphenylhydrazine HCl (80.32 g.) was reacted with 3-amino-2-butene nitrile (32.5 g.) as described in Example XLIII to give 60.5 g. product, mp 86°-87°.

Analyzed for $C_{11}H_{12}ClN_3$: Theoretical; C=59.59, H=5.45, N=18.95. Found; C=59.44, H=5.49, N=18.73.

EXAMPLE LX

1-Acetyl-2[1(4-chloro-2-methylphenyl)-3-methyl-5-pyrazolyl] amino-2-imidazoline

5-Amino-3-methyl-1-(4-chloro-2-methylphenyl) pyrazole (22.16 g.) and 1-acetyl-2-imidazolinone (15.4 g.) were reacted as described in Example I to give 13.1 g. of product, mp 195°-195°.

Analyzed for $C_{16}H_{18}ClN_5O$: Theoretical; C=57.91, H=5.96, N=21.10. Found; C=57.87, H=5.52, N=21.14.

EXAMPLE LXI

2-[1(4-chloro-2-methylphenyl)-3-methyl-5-pyrazolyl] amino-2-imidazoline HCl

1-Acetyl-2[1-(4-chloro-2-methylphenyl)-3-methyl-5-pyrazolyl] amino-2-imidazoline (10.0 g.) was treated with HCl in methanol as described in Example II to give 7.4 g. product as the HCl salt, mp 134°-135°.

Analyzed for $C_{14}H_{16}ClN_5 \cdot HCl$: Theoretical; C=51.54, H=5.25, N=21.47. Found; C=51.70, H=5.18, N=21.56

EXAMPLE LXII

1-Acetyl-2(1-methyl-3-phenyl-5-pyrazolyl) amino-2-imidazoline

5-Amino-1-methyl-3-phenylpyrazole (17.3 g.) and 1-acetyl-2-imidazolinone (15.4 g.) were reacted as described in Example I to give 14.0 g. product, mp 154°-155°.

Analyzed for $C_{15}H_{17}N_5O$: Theoretical; C=63.58, H=6.04, N=24.71. Found; C=63.79, H=6.22, N=24.95.

EXAMPLE LXIII

2(1-Methyl-3-phenyl-5-pyrazolyl)-amino-2-imidazoline hydrochloride

1-Acetyl-2-(1-methyl-3-phenyl-5-pyrazolyl)amino-2-imidazoline (10.0 g.) was treated with HCl in methanol as described in Example II to give 5.5 g. of product as the HCl salt, mp 195°-197°.

Analyzed for $C_{13}H_{15}N_5 \cdot HCl$: Theoretical; C=56.21, H=5.80, N=25.21. Found; C=56.01, H=5.85, N=25.24.

EXAMPLE LXIV

1-Acetyl-2[1-(4-methoxyphenyl)-3-methyl-5-pyrazolyl]amino-2-imidazoline

5-Amino-3-methyl-1-(4-methoxyphenyl) pyrazole HCl (Farmaco 17, 443, 1962) (23.9 g.) and 1-acetyl-2-imidazolinone (15.4 g.) were reacted as described in Example I to give 14.6 g. of product, mp 129°-131°.

Analyzed for $C_{16}H_{19}N_5O_2$: Theoretical; C=61.32, H=6.11, N=22.34. Found; C=60.87, H=6.15, N=22.05.

EXAMPLE LXV

2-[1-(4-Methoxyphenyl)-3-methyl-5-pyrazolyl]amino-2-imidazoline HCl

1-Acetyl-2[1-(4-methoxyphenyl)-3-methyl-5-pyrazolyl]amino-2-imidazoline (13.1 g.) was treated with HCl in methanol as described in Example II to give 7.9 g. of product as the HCl salt, mp 197°-198°.

Analyzed for $C_{14}H_{17}N_5O \cdot HCl$: Theoretical; C=54.63, H=5.89, N=22.75. Found; C=54.77, H=5.97, N=22.91.

EXAMPLE LXVI

1-Acetyl-2-[1-(3-chlorophenyl)-3-methyl-5-pyrazolyl]amine-2-imidazoline

5-Amino-3-methyl-1-(3-chlorophenyl)pyrazole (Farmaco, 19, 638, 1964) (31.14 g.) and 1-acetyl-2-imidazolinone (23.06 g.) were reacted as described in Example I to give 25.1 g. product, mp 140°-141°.

Analyzed for $C_{15}H_{16}ClN_5O$: Theoretical; C=56.69, H=5.07, N=22.03. Found; C=56.53, H=5.12, N=22.13.

EXAMPLE LXVII

2-[1-(3-chlorophenyl)-3-methyl-5-pyrazolyl]amino-2-imidazoline HCl

1-Acetyl-2-[1-(3-chlorophenyl)-3-methyl-5-pyrazolyl]amino-2-imidazoline (19.7 g.) was treated with HCl in methanol as described in Example II to give 6.5 g. product as the HCl salt, mp 208°–209°.

Analyzed for $C_{13}H_{14}ClN_5 \cdot HCl$: Theoretical; C=50.01, H=4.84, N=22.43. Found; C=50.43, H=4.76, N=22.39.

EXAMPLE LXVIII

1-Acetyl-2[1-(2-methylphenyl)-3-methyl-5-pyrazolyl]amino-2-imidazoline

5-Amino-3-methyl-1-(2-methylphenyl)pyrazole HCl (Farmaco, 19, 638, 1964) (26.5 g.) and 1-acetyl-2-imidazolinone (18.2 g.) were reacted as described in Example I to give 12.6 g. product, mp 160°–161°.

Analyzed for $C_{16}H_{19}N_5O$: Theoretical; C=64.62, H=6.44, N=23.55. Found; C=64.14, H=6.27, N=23.57.

EXAMPLE LXIX

2[1-(2-Methylphenyl)-3-methyl-5-pyrazolyl]amino-2-imidazoline

1-Acetyl-2-[1-(2-methylphenyl)-3-methyl-5-pyrazolyl]amino-2-imidazoline (7.0 g.) was treated with HCl in methanol as described in Example II to give 4.6 g. of product, mp 168°–169°.

Analyzed for $C_{14}H_{17}N_5$: Theoretical; C=65.85, H=6.71, N=27.42. Found; C=65.73, H=6.78, N=27.77.

EXAMPLE LXX

5-Amino-3-methyl-1-(3,4-dichlorophenyl)pyrazole 3,4-Dichlorophenyl hydrazene HCl (50.0 g.) was reacted with 3-amino-2-butene nitrile (18.31 g.) as described in Example XLIII to give 18.7 g. product, mp 110°–112°.

Analyzed for $C_{10}H_9Cl_2N_3$; Theoretical; C=49.61, H=3.74, N=17.35 Found; C=50.09, H=3.75, N=17.43

EXAMPLE LXXI

1-Acetyl-2[1-(3,4-dichlorophenyl)-3-methyl-5-pyrazolyl]amino-2-imidazoline

5-Amino-3-methyl-1-(3,4-dichlorophenyl)pyrazole (16.6 g.) and 1-acetyl-2-imidazolinone (10.6 g.) were reacted as described in Example I to give 8.5 g. of product, mp 156°–157°.

Analyzed for $C_{15}H_{15}Cl_2N_5O$: Theoretical; C=51.15, H=4.29, N=19.88. Found; C=51.16, H=4.37, N=19.82.

EXAMPLE LXXII

2[1-3,4-dichlorophenyl)-3-methyl-5-pyrazolyl]amino-2-imidazoline HCl

1-Acetyl-2[1,-(3,4-dichlorophenyl)-3-methyl-5-pyrazolyl]amino-2-imidazoline (7.0 g.) was treated with HCl in methanol as described in Example II to give 2.7 g. of product as the HCl salt, mp 266°–267°.

Analyzed for $C_{13}H_{13}Cl_2N_5 \cdot HCl$: Theoretical; C=40.04, H=4.07, N=20.20. Found; C=45.32, H=4.18, N=20.42.

EXAMPLE LXXIII

1-Acetyl-2-(1-benzyl-3-methyl-5-pyrazolyl)amino-2-imidazoline

5-Amino-1-benzyl-3-methylpyrazole (J. Gen. Chem. USSR, 31, 2307, 1961) (17.0 g.) and 1-acetyl-3-imidazolinone (14.0 g.) were reacted as described in Example I to give 11.7 g. of product, mp 148°–149°.

Analyzed for $C_{16}H_{19}N_5O$: Theoretical; C=64.63, H=6.44, N=23.55. Found; C=64.83, H=6.55, N=23.82.

EXAMPLE LXXIV

2(1-Benzyl-3-methyl-5-pyrazolyl)amino-2-imidazoline HCl

1-Acetyl-2-(1-benzyl-3-methyl-5-pyrazolyl)amino-2-imidazoline (12.5 g.) was treated with HCl in methanol as described in Example II to give 7.2 g. of product, mp 198°–199°, (as the HCl salt).

Analyzed for $C_{14}H_{17}N_5 \cdot HCl$: Theoretical; C=57.63, H=6.22, N=24.00 Found; C=57.76, H=6.33, N=24.03

EXAMPLE LXXV

2-[1-(4-Hydroxhphenyl)-3-methyl-5-pyrazolyl]amino-2-imidazoline hydrochloride

2-[1-(4-methoxyphenyl)-3-methyl-5-pyrazolyl]amino-2-imidazoline hydrochloride (3.0 g.) was refluxed with 75 ml. 48% HBr for 16 hours. Addition of ammonia gave a solid which was converted to the hydrochloride with •HCl giving 1.50 g. product mp 286°–287°.

Analyzed for $C_{13}H_{15}N_5O \cdot HCl$: Theoretical; C=53.15, H=4.59, N=23.84 Found; C=52.72, H=5.62, N=23.67

By the methods described in the proceeding examples, the following compounds were synthesized:

(a) 2-(1-benzyl-5-pyrazolyl) amino-2-imidazoline HCl, mp 141°–143°.

(b) [1-(3-nitrophenyl)-3-methyl-5-pyrazolyl]amino-2-imidazoline HCl, mp 218°–220°.

(c) 2-(3,4-dimethyl-1-phenylpyrazolyl)amino-2-imidazoline HCl, mp 209°–210°.

(d) 2(1,4-Diphenyl-3-methylpyrazolyl)amino-2-imidazoline HCl, mp 252°–254°.

(e) 2(1,3-dimethyl-4-phenylpyrazolyl)amino-2-imidazoline HCl, mp 249°–251°.

(f) 2[1-(2-biphenylyl)-3-methylpyrazolyl]amino-2-imidazoline, mp 204°–205°.

(g) 2[3-methyl-1-(3-quinolinyl)pyrazolyl]amino-2-imidazoline, mp 190°–192°.

EXAMPLE LXXVI

1-Methyl-2(1,3-dimethyl-5-pyrazolyl)amino-2-imidazoline

N(1,3-Dimethyl-5-pyrazolyl)-5-methyl isothiourea hydroiodide (Example XXV) (20.0 g) and 11.5 g. N-methyl ethylenediamine were heated to 120° for 30 minutes and to 160° for 1 hour. After cooling, methylene chloride was added and the solid which formed was filtered and discarded. The methylene chloride solution was shaken with 15% KOH solution, dried over potassium carbonate, concentrated and the residue crystallized from acetonitrile to get 10.16 g. product, mp 128°–130°.

Analyzed for $C_9H_{15}N_5$: Theoretical; C=55.93, H=7.82, N=36.24. Found; C=55.78, H=7.95, N=36.05.

The antihypertensive activity of the compounds of this invention was established in genetically hypertensive (SH) rats. In this test, adult male SH rats of the Okamoto strain were trained to be restrained in a wire mesh cylinder for measurement of blood pressure. One half hour prior to blood pressure measurement, the rats were placed in a warm chamber maintained at a constant temperature of 36° C. An occluding cuff, attached to a programmed sphygmomanometer, was placed near the base of the tail of each rat and the pressure in the cuff was increased automatically from 0 to 250 mm Hg at a rate of 10 mm Hg per second. The cuff was then deflated at the same rate. The total time required for each cycle of inflation and deflation of the cuff was 50 seconds and the interval between successive cycles was one minute. A photocell was placed distal to the cuff to sense the arterial pulse wave. As the pressure in the cuff increased, the pulse wave completely disappeared when the cuff pressure just exceeded the systolic arterial blood pressure. During deflation, the pulse wave reappeared at approximately the same pressure. Five interference-free signals obtained during deflation were recorded for each rat. Only those rats with a systolic blood pressure of 180 mm Hg or more during the control period were used in this study. A model 7 Grass polygraph was used to record the cuff pressure and the arterial pulse wave. The heart rate of the rat was computed from the record of the arterial pulse wave. The compounds tested were administered orally to the rats, the results recorded below in Table I. From Table I it can be seen that the compounds exhibited significant antihypertensive activity.

The compounds of the present invention can be incorporated into pharmaceutically acceptable dosage forms such as suspensions, tablets, capsules, and the like for either immediate or sustained release. By combining them with suitable carriers or diluents using conventional methods known in the art. In addition to the active agent and the carrier or diluent, the dosage forms may include various binders, excipients, fillers, or flavoring agents to provide a satisfactory formulation of the desired pharmaceutical preparation.

What is claimed is:

1. A method of treating hypertension in mammalian patients in need of such treatment which comprises administering to said patients a therapeutically effective amount of a compound of the formula

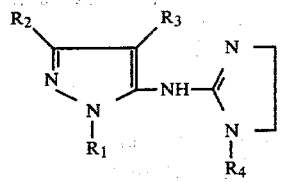

wherein $R_1$ and $R_2$ are hydrogen, loweralkyl, lowercycloalkyl, benzyl, phenyl or naphthyl, pyridyl, isoquinolyl or phthalazinyl, or phenyl or naphthyl substituted by one or more hydrogen, halo, loweralkyl, lowercycloalkyl, haloloweralkyl, aminosulfonyl, nitro, hydroxy, alkoxy, carboxy, alkoxycarbonyl, cycloalkoxy carbonyl, aminocarbonyl, diloweralkylaminocarbonyl or

wherein n is 4 or 5

$R_3$ is hydrogen, halogen, loweralkyl, phenyl or naphthyl, and $R_4$ is hydrogen, acetyl, amino or loweralkyl, or the pharmaceutically acceptable acid addition salts thereof.

2. A method according to claim 1 wherein $R^1$ and $R^2$ are each hydrogen, alkyl, cycloalkyl, phenyl or naph-

TABLE I
ANTIHYPERTENSIVE EFFECT, LOWERING IN BLOOD PRESSURE

| | Compound | | | Dose, | Time, | % Decrease |
|---|$R_1$|$R_2$|$R_3$|$R_4$|mg.|hr.|in b.p.|
| 1. | $CH_3$ | H | H | H | 10 | 1 | 19 |
| | | | | | 3 | 6 | 10 |
| 2. | $CH_3$ | H | $CH_3$ | H | 30 | 4 | 44 |
| 3. | $CH_3$ | H | Br | H | 30 | 4 | 19 |
| 4. | $CH_3$ | H | $C_6H_5$— | H | 30 | 4 | 37 |
| 5. | $CH_3$ | $CH_3$ | H | H | 1 | 1 | 21 |
| | | | | | 0.3 | 1 | 11 |
| 6. | $CH_3$ | $CH_3$ | Br | H | 0.3 | 6 | 13 |
| 7. | $CH_3$ | $CH_3$ | I | H | 10 | 6 | 49 |
| 8. | $C_6H_5$— | $C_6H_5$— | H | H | 100 | 4 | 12 |
| 9. | $C_6H_5$— | $C_6H_5$— | Br | H | 100 | 4 | 18 |
| 10. | $C_6H_5$— | H | H | H | 10 | 6 | 20 |
| 11. | $(CH_3)_2CH$— | $(CH_3)_2CH$— | H | H | 100 | 4 | 12 |
| 12. | $C_6H_5$ | H | Br | H | 30 | 4 | 42 |
| 13. | $(CH_3)_2CH$— | $(CH_3)_2CH$— | Br | H | 10 | 24 | 17 |
| 14. | $CH_3$ | $(CH_3)_2CH$— | H | H | 30 | 4 | 26 |
| 15. | $CH_3$ | $(CH_3)_2CH$ | Br | H | 100 | 4 | 37 |
| 16. | $(CH_3)_2CH$— | $CH_3$ | H | H | 30 | 6 | 15 |
| 17. | $(CH_3)_2CH$— | $CH_3$ | Br | H | 100 | 4 | 12 |
| 18. | $C_6H_5$ | H | H | $COCH_3$ | 30 | 4 | 38 |
| 19. | $CH_3$ | $(CH_3)_2CH$— | H | $COCH_3$ | 100 | 4 | 17 |
| 20. | $(CH_3)_2CH$ | $CH_3$ | H | $COCH_3$ | 100 | 4 | 13 |
| 21. | $CH_3$ | H | H | $COCH_3$ | 100 | 4 | 16 |
| 22. | $CH_3$ | $CH_3$ | $CH_3$ | $COCH_3$ | 10 | 6 | 14 |
| 23. | $CH_3$ | $CH_3$ | H | $COCH_3$ | 30 | 4 | 19 | thyl, $R^3$ is hydrogen or halogen, $R^4$ is hydrogen or acetyl, or pharmaceutically acceptable acid addition salts thereof.

3. A method according to claim 1 wherein $R^1$ and $R^2$ are each hydrogen, loweralkyl or phenyl, $R^3$ is hydrogen, chloro, bromo or iodo, and $R^4$ is hydrogen or acetyl, or pharmaceutically acceptable acid addition salts thereof.

4. A method according to claim 2 wherein $R^1$ is methyl or phenyl, $R^2$ is hydrogen, methyl, or ethyl, $R^3$ is hydrogen, chloro, bromo, or iodo and $R^4$ is hydrogen or acetyl.

5. A method according to claim 3 wherein $R^1$ is phenyl, and $R^2$, $R^3$ and $R^4$ are each hydrogen.

6. A method according to claim 3 wherein $R^1$ is methyl, $R^2$ is methyl, $R^3$ is chloro, and $R^4$ is hydrogen, or the hydrochloride salt thereof.

7. A method according to claim 3 wherein $R^1$ is methyl, $R^2$ is methyl, $R^3$ is chloro, and $R^4$ is acetyl, or the hydrochloride salt thereof.

8. A method according to claim 4 wherein $R^1$ is phenyl, $R^2$ is hydrogen, $R^3$ is hydrogen, and $R^4$ is acetyl.

9. A method according to claim 1 wherein $R_1$ and $R_2$ are hydrogen, loweralkyl, haloloweralkyl, benzyl, naphthyl, pyridyl, isoquinolyl, phthalazinyl, phenyl or naphthyl substituted by one or more hydrogen, halo, loweralkyl, lowercycloalkyl, haloloweralkyl, aminosulfonyl, nitro, hydroxy, alkoxy, carboxy, alkoxycarbonyl, cycloalkoxycarbonyl, aminocarbonyl, diloweralkylaminocarbonyl

wherein n is 4 or 5,
$R_3$ is hydrogen, loweralkyl, phenyl or naphthyl, and
$R_4$ is hydrogen, acetyl, amino or loweralkyl, with the proviso that $R_4$ cannot be hydrogen or acetyl when $R_1$ and $R_2$ are each H, loweralkyl or phenyl and $R_3$ is hydrogen.

* * * * *